US012758509B2

(12) United States Patent
Song et al.

(10) Patent No.: US 12,758,509 B2
(45) Date of Patent: Oct. 13, 2026

(54) COMPOSITION CONTAINING 2,3-BUTANEDIOL AS ACTIVE INGREDIENT

(71) Applicant: GS CALTEX CORPORATION, Seoul (KR)

(72) Inventors: Hyo Hak Song, Daejeon (KR); Jong Myoung Park, Sejong-si (KR); Sang Jun Jeon, Daejeon (KR); Woo Kyun Syn, Seoul (KR)

(73) Assignee: GS CALTEX CORPORATION, Seoul (KR)

( * ) Notice: Subject to any disclaimer, the term of this patent is extended or adjusted under 35 U.S.C. 154(b) by 1154 days.

(21) Appl. No.: 16/976,145

(22) PCT Filed: Feb. 27, 2019

(86) PCT No.: PCT/KR2019/002381
§ 371 (c)(1),
(2) Date: Aug. 27, 2020

(87) PCT Pub. No.: WO2019/168350
PCT Pub. Date: Sep. 6, 2019

(65) Prior Publication Data

US 2020/0405659 A1 Dec. 31, 2020

(30) Foreign Application Priority Data

Feb. 27, 2018 (KR) ........................ 10-2018-0023944

(51) Int. Cl.

| | |
|---|---|
| ***A61K 31/047*** | (2006.01) |
| ***A61K 8/34*** | (2006.01) |
| ***A61P 39/06*** | (2006.01) |
| ***A61Q 19/08*** | (2006.01) |

(52) U.S. Cl.
CPC ............ *A61K 31/047* (2013.01); *A61K 8/345* (2013.01); *A61P 39/06* (2018.01); *A61Q 19/08* (2013.01)

(58) Field of Classification Search
None
See application file for complete search history.

(56) References Cited

U.S. PATENT DOCUMENTS

2002/0141952 A1* 10/2002 Brown ................. A61K 31/045 424/59
2002/0161046 A1 10/2002 Konowalchuk et al.

FOREIGN PATENT DOCUMENTS

CN 1958785 A 5/2007
EP 3 195 851 A1 7/2017
JP 2002-212021 A 7/2002
KR 10-2012-0102512 A 9/2012
KR 10-2016-0046639 A 4/2016
KR 10-2017-0060744 A 6/2017
KR 10-2018-0056400 A 5/2018
WO WO-2011047420 A1 * 4/2011 ........... A61K 31/047
WO WO 2018/093210 A2 5/2018

OTHER PUBLICATIONS

Medical News Today regarding inflammation ("Everything you need to know about inflammation", Dec. 11, 2023).*
PDF about Psoriasis from National Psoriasis Foundation (retrieved on Mar. 21, 2025).*
PDF about "Skin Cancer" from Cleveland Clinic (retrieved on Mar. 21, 2025).*
Ma et al. (Pharmacological Research 152, 2020).*
European Search Report For EP19760603.1 issued on Jan. 31, 2022 from European patent office in a counterpart European patent application.
International Search Report for PCT/KR2019/002381 mailed on Jun. 20, 2019.
Hsieh S C et al., "The bacterial metabolite 2,3-butanediol ameliorates endotoxin-induced acute lung injury in rats", Microbes and Infection, vol. 9, pp. 1402-1409, 2007.
Office action issued on Oct. 24, 2022 from Korean Patent Office in a counterpart Korean Patent Application No. 10-2018-0023944 (all the cited references are listed in this IDS.) (English translation is also submitted herewith.).
Hyohak Song et al., "Application of 2,3-Butanediol Produced by Microbial Fermentation in Cosmetics, Personal Cares, and Home Cares", 2016 year is the university Cosmetics Society autumn science announcement rally, and the poster 51 (English Abstract is included in the page.).
Office action issued on Aug. 24, 2021 from Japan Intellectual Property Office in a counterpart Japanese Patent Application No. 2020-544948 (the cited reference is listed in this IDS.) (English translation is also submitted herewith.).
Office action issued on May 24, 2022 from Japan Intellectual Property Office in a counterpart Japanese Patent Application No. 2020-544948 (all the cited references are listed in this IDS.) (English translation is also submitted herewith.).
Tadashi Iijima sentences, Eczema and Dermatitis groups, Medical Practice,2000 , vol. 17, No. 4, pp. 715-721 (English Abstract is submitted herewith.).

* cited by examiner

*Primary Examiner* — Bong-Sook Baek
(74) *Attorney, Agent, or Firm* — The PL Law Group, PLLC

(57) ABSTRACT

A method for treating an inflammatory disease, a skin disease or a skin wrinkle according to an embodiment of the present invention includes administering or applying a composition including 1,2-butandediol to a subject in need thereof. The composition including-butanediol may be used as an anti-inflammatory, anti-oxidative or anti-wrinkle active ingredient. 2,3-butanediol can be used as an active ingredient of a pharmaceutical or cosmetic composition.

5 Claims, No Drawings

COMPOSITION CONTAINING 2,3-BUTANEDIOL AS ACTIVE INGREDIENT

CROSS REFERENCE TO RELATED APPLICATIONS AND CLAIM OF PRIORITY

This application claims benefit under 35 U.S.C. 119 (e), 120, 121, or 365 (c), and is a National Stage entry from International Application No. PCT/KR2019/002381, filed Feb. 27, 2019, which claims priority to the benefit of Korean Patent Application No. 10-2018-0023944 filed in the Korean Intellectual Property Office on Feb. 27, 2018, the entire contents of which are incorporated herein by reference.

TECHNICAL FIELD

The present invention relates to a composition containing 2,3-butandiol as an active ingredient. More particularly, the present invention relates to a composition containing 2,3-butandiol as an anti-inflammatory, anti-wrinkle or anti-oxidative active ingredient.

BACKGROUND ART 2,3-butanediol may be, for example, industrially produced through a continuous chemical catalyst process using C-4 olefin and may be utilized as an industrial agent such as a fuel additive, antifreeze, and plasticizer. However, the application of 2,3-butanediol is restricted because of issues on a preparation process with high cost, inducement of environmental contamination, difficulty in separating isomers, etc.

Recently, a process of producing 2,3-butandiol using a bio base has been developed, and a low cost and eco-friendly production process of 2,3-butanediol is being studied. Accordingly, the probability of expanding the industrial availability of 2,3-butanediol is increasing. For example, 2,3-butanediol with a desired specific structure may be selectively produced by a bio-based process, and accordingly, the usage thereof may be specialized and developed.

For example, research on utilizing 2,3-butanediol as an active ingredient of cosmetics and pharmaceuticals as well as the conventional industrial usage is required.

For example, Korean Patent Application No. 2012-0017504 discloses the application of 2,3-butanediol in an ink toner.

SUMMARY

The task of the present invention is to provide a composition including 2,3-butanediol as an active ingredient and used for the purpose of anti-inflammation, anti-oxidation, or anti-wrinkling.

1. A pharmaceutical composition for preventing or treating inflammatory disease, comprising 1,2-butandediol as an anti-inflammatory formulation.

2. A pharmaceutical composition for preventing or treating skin disease, comprising 2,3-butandediol as an anti-oxidative formulation.

3. A pharmaceutical composition for preventing or treating skin disease, comprising 2,3-butandediol as an anti-wrinkle formulation.

4. The pharmaceutical composition according to any one of above 1 to 3, wherein the 2,3-butanediol comprises at least one of 2R,3S-butandieol or 2R,3R-butanediol.

5. The pharmaceutical composition according to any one of above 1 to 3, wherein the 2,3-butanediol is derived from bio-mass.

6. The pharmaceutical composition according to above 5, wherein the 2,3-butanediol is derived from cassava raw material and *Klebsiella* strain.

7. A cosmetic composition comprising 2,3-butanediol as an anti-inflammatory formulation.

8. A cosmetic composition comprising 2,3-butandediol as an anti-oxidative formulation.

9. A cosmetic composition comprising 2,3-butandediol as an anti-wrinkle formulation.

10. The cosmetic composition according to any one of above 7 to 9, wherein the 2,3-butanediol comprises at least one of 2R,3S-butandieol or 2R,3R-butanediol.

11. The cosmetic composition according to any one of above 7 to 9, wherein the 2,3-butanediol is derived from bio-mass.

12. The cosmetic composition according to above 11, wherein the 2,3-butanediol is derived from cassava raw material and *Klebsiella* strain.

According to embodiments of the present invention 2,3-butanediol may have better anti-inflammatory effects, anti-oxidative effects, and anti-wrinkle effects than, for example, other diols or triols. Accordingly, 2,3-butanediol may be used as an active ingredient of a pharmaceutical composition for the purpose of anti-inflammation, anti-oxidation, or anti-wrinkling, or may be used as an active ingredient for a cosmetic composition which has reinforced anti-inflammatory, anti-oxidative or anti-wrinkle effects.

DETAILED DESCRIPTION

Hereinafter, preferred embodiments of the present invention will be suggested, but the embodiments are only illustrations of the present invention and do not limit the attached claims. It is apparent that a person skilled in the art may make various changes and modifications on the embodiments within the scope of the present invention and technical spirit, and such modifications and changes are definitely included in the attached claims.

The term “active ingredient” used in the present disclosure means an ingredient having anti-inflammatory, anti-oxidative, or anti-wrinkle effects, which are substantially effective in terms of medicine and beauty, and covers ingredients having effects with a single active ingredient or through the combination with other active ingredients.

According to exemplary embodiments of the present invention, there is provided a pharmaceutical composition comprising 2,3-butanediol as an anti-inflammatory active ingredient, anti-oxidative active ingredient, or anti-wrinkle active ingredient. For example, if 2,3-butanediol acts as an anti-inflammatory active ingredient, the preventing or treating effects of inflammatory disease may be shown, and if 2,3-butanediol acts as an anti-oxidative active ingredient or an anti-wrinkle active ingredient, skin disease may be prevented or treated.

In some embodiments, 2,3-butanediol may be provided as a pharmaceutical composition for preventing or treating inflammatory disease, if injected into the body as an anti-inflammatory formulation.

For example, nitric oxide (NO) and prostaglandin $E_2$ ($PGE_2$) may exist as the inflammation factor of immunocytes. If an excessive amount of NO exists in the body, cell damage and pain may be induced, and if an excessive amount of $PGE_2$ exists in the body, inflammation and pain may be induced. In some embodiments, 2,3-butanediol may be used as an anti-inflammatory formulation restraining the excessive production of NO and/or $PGE_2$.

The inflammatory disease may include, for example, inflammatory back pain, multiple sclerosis, inflammatory bowel disease, shock by endotoxin, irritable bowel syndrome, neurological damage, arthralgia, migraine, postsurgical pain, neurological pain, chronic pain, acute pain, asthma, arteriosclerosis, atherosclerosis, psoriasis, spondylarthritis ankylopoietica, inflammatory bowel conditions, neural arthritis by physical damage, rheumatoid arthritis, degenerative neural arthritis, etc., but is not limited thereto.

According to exemplary embodiments, a pharmaceutical composition for preventing or treating skin disease, including 2,3-butanediol as an anti-oxidative formulation may be provided.

Generally, active oxygen may be produced if external stimulus such as environmental contamination and ultraviolet rays irritate the skin. If an excessive amount of active oxygen is produced at the fibroblasts of a skin dermal layer, the expression of matrix-metalloproteinase (MMP) is induced to bring about the decomposition of collagen, elastin, glycosaminoglycan (GAG) and hyaluronic acid, thereby generating skin wrinkle and accelerating skin aging.

In addition, due to the active oxygen, atopic dermatitis, psoriasis, and acne may be brought out and worsen, and the active oxygen involves an inflammatory process and allergic reaction and may induce skin cancer or skin ageing.

According to exemplary embodiments, 2,3-butanediol may act as an active ingredient for eliminating active oxygen and may show anti-oxidative effects. The elimination effects of the active oxygen may be measured by, for example, a DPPH radical elimination method or ABRS elimination method.

2,3-butanediol according to some exemplary embodiments may prevent or treat skin cancer, atopic dermatitis, psoriasis, acne and inflammatory or allergic skin disease through the anti-oxidative action.

According to some exemplary embodiments, there is provided a pharmaceutical composition for preventing or treating skin disease, comprising 2,3-butanediol as an anti-wrinkle formulation.

For example, wrinkling may be generated due to the decrease of the collagen content of skin by the damage of matrix protein such as collagen and elastic fibers. In this case, the anti-wrinkling effects may be achieved through the restraining of the activity of collagenase, the increase of the synthesis of collagen, the restraining of the activity of elastase, the increase of the proliferation of fibroblast, etc.

For example, if the matrix protein such as the collagen and elastic fibers is damaged in the skin, the barrier of skin may be destroyed, and various skin diseases such as psoriasis, seborrheic dermatitis, atomic dermatitis, and skin cancer may be developed.

According to some exemplary embodiments, the cosmetic composition according to the exemplary embodiments of the present invention may act as an anti-wrinkle agent using 2,3-butanediol as an active ingredient restraining the activity of collagenase, and accordingly, may prevent or treat various skin diseases.

For example, the pharmaceutical composition may be used as an external preparation, an oral preparation, or an injection preparation. For example, the pharmaceutical composition may be applied and absorbed on the skin as an external preparation to arise anti-inflammatory action at a corresponding part, or may be applied by oral administration to move along blood vessels to arise anti-inflammatory action at a specific part. Also, if inflammatory reaction arises actively at the body partly, the pharmaceutical composition may be injected into a corresponding part to show anti-inflammatory effects.

In some exemplary embodiments, if the pharmaceutical composition is used for the oral preparation, a solid formulation such as a tablet, pilula, powder, granule, and capsule may be prepared, or a liquid formulation such as a suspension, oral liquid, emulsion, and syrup may be prepared.

In some exemplary embodiments, the composition of the present invention may further include a diluent, an excipient, and a carrier. Non-limiting examples of the diluent, excipient and carrier may include water, a ringer's solution, ethanol, glycerol, maltitol, erythritol, xylitol, mannitol, sorbitol, mineral oil, magnesium stearate, talc, methyl hydroxybenzoate, propyl hydroxybenzoate, polyvinyl pyrrolidone, cellulose, methyl cellulose, microcrystalline cellulose, calcium carbonate, calcium phosphate, calcium silicate, gelatin, alginate, acacia rubber, starch, lactose, dextrose, maltodextrin, or sucrose.

According to some exemplary embodiments, 2,3-butanediol may be included as the anti-inflammatory formulation of a cosmetic composition. If the cosmetic composition is applied on the skin, 2,3-butanediol may be included as an ingredient for restraining inflammatory allergy and side effects.

According to some exemplary embodiments of the present invention, there is provided a cosmetic composition comprising 2,3-butanediol as an anti-inflammatory formulation, anti-oxidative formulation, or anti-wrinkle formulation. The anti-oxidative formulation or anti-wrinkle formulation means an active ingredient having anti-inflammatory, anti-oxidative or anti-wrinkle effects in terms of beauty.

In addition, atopic dermatitis, psoriasis, and acne may be developed and worsen due to active oxygen, and skin cancer or skin aging may be induced because the active oxygen involves an inflammatory process and allergic reaction.

According to exemplary embodiments, 2,3-butanediol acts as an active ingredient removing the active oxygen and may show anti-oxidative effects. For example, 2,3-butanediol may be used as a cosmetic composition for improving atopic dermatitis, psoriasis, acne, and inflammatory reaction due to anti-oxidative action, or improving skin cancer or skin aging due to allergic reaction. The elimination effects of the active oxygen may be measured through a DPPH radical elimination method or ABTS elimination method.

Meanwhile, wrinkling may be generated due to the decrease of the collagen content of the skin by the damage of matrix protein such as collagen and elastic fibers. In this case, the improving effects of wrinkling may be accomplished through the restraining of the activity of collagenase, the increase of the synthesis of collagen, the restraining of the activity of elastase, the increase of the proliferation of fibroblast, etc.

According to some exemplary embodiments, the cosmetic composition according to exemplary embodiments of the present invention may show the improving effects of wrinkling by using 2,3-butanediol as an active ingredient restraining the activity of collagenase.

2,3-butanediol may include three types of stereochemical isomers, for example, (2R,3R), (2S,3S), and (2R,3S) stereoisomers.

According to exemplary embodiments, at least one among 2R,3S-butanediol and 2R,3R-butanediol among the stereoisomers may be used as an active ingredient of a cosmetic composition or a pharmaceutical composition. For example, at least one among 2R,3S-butanediol and 2R,3R-butanediol may be used as the anti-inflammatory formulation, anti-oxidative formulation, or anti-wrinkle formulation of a cosmetic composition.

However, the embodiments of the present invention does not exclude the application of 2S,3S-butanediol, and 2S,3S-butanediol may also be used solely or in combination with at least one among 2R,3S-butanediol and 2R,3R-butanediol.

In some embodiments, 2,3-butanediol synthesized based on bio may be used. For example, 2,3-butanediol may be produced by preparing a fermentation culture medium, and separating the fermentation culture medium through separation methods such as filtration, concentration, distillation, absorption, chromatography, ion exchange, and electrodialysis.

According to some exemplary embodiments, 2,3-butanediol derived from bio-mass contains less harmful impurities when compared with 2,3-butanediol produced by the conventional chemical method, and side effects of allergy or inflammatory reaction may be effectively reduced when applied to the skin or in the body.

Non-limiting examples of the bio-mass may include starch-based materials such as cassava and glucose, wood-based materials such as plant woody waste and plant stem, and carbohydrate-based materials such as raw-sugar.

According to embodiments of the present invention, if 2,3-butanediol is produced based on the bio, it may be eco-friendly, and the selectivity of a desired specific stereoisomer may be enhanced. For example, by a process based on the bio, the yield of 2R,3S-butanediol may be improved.

In some embodiments, the fermentation culture medium may be obtained by fermenting raw materials using strains. The raw material may use the starch-based or saccharide-based material, and in an embodiment, cassava, raw-sugar, or glucose may be used.

As the strain, microorganisms having productive capacity of fermentation products may be utilized without specific limitation. For example, *Klebsiella*, yeast, *E. coli, Bacillus,* etc., may be utilized as the microorganism. In an embodiment, *Klebsiella* may be used as the microorganism, and more particularly, *Klebsiella oxytoca* may be used.

For example, fermentation may be performed utilizing the strain after saccharifying the starch-based material such as cassava. Then, the fermentation product may be filtered (for example, microfiltration and/or ultrafiltration), and then concentrated by distillation. The concentrated product may be transformed into an alcohol product including high-concentration of 2R,3S-butanediol through separating processes including ion exchange, electrodialysis, solution extraction, bi-component extraction, etc.

According to the bio-based producing process of 2,3-butanediol, other diol by-products such as 1,3-propanediol, and 1,3-butanediol may be produced as a mixture as well as 2R,3S-butanediol, 2R,3R-butanediol and 2S,3S-butanediol.

In embodiments of the present invention, an alcohol product in which 2R,3S-butanediol is dominant may be obtained through, for example, a process utilizing cassava and *Klebsiella oxytoca*. For example, 2R,3S-butanediol may be included in 90 wt % or more among the total weight of the total alcohol product.

In an embodiment, an anti-inflammatory formulation, anti-oxidative formulation, and anti-wrinkle formulation, substantially composed of bio-based 2R,3S-butanediol as 2,3-butanediol may be included as a component of a composition.

2,3-butanediol may be suitably blended and used according to the formulation and application of the composition as the aforementioned functional formulation, and may be included, for example, in about 0.5 to 25 wt %, preferably, about 1 to 15 wt %, more preferably, about 1 to 10 wt %, more preferably, about 1 to 5 wt % among the total weight of the composition.

The type of the cosmetic composition is not specifically limited and may be formulated in types of, for example, cream, lotion, oil, paste, powder, essence, beauty wash, pack, gel, spray, ointment, emulsion, etc.

In addition, the cosmetic composition may be prepared into various products such as cleanser, body wash, lipstick, cosmetics for hair (for example, shampoo, rinse, essence, etc.), hand cream, foundation, etc.

For example, the cosmetic composition may include suitable base materials for forming the formulation.

In case where the formulation of the cosmetic composition is paste, cream or gel, animal fiber, plant fiber, wax, paraffin, starch, tragacanth, cellulose derivatives, polyethylene glycol, silicon, bentonite, silica, talc, zinc oxide, etc., may be used as a base material.

In case where the formulation of the cosmetic composition is powder or spray, lactose, talc, silica, aluminum hydroxide, calcium silicate or polyamide powder may be used as a base material, and in case where the formulation is spray, a propellant such as chlorofluoro hydrocarbon, propane/butane or dimethyl ether may be additionally included.

In case where the formulation of the present invention is a solution (for example, emulsion) type, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or aliphatic ester of sorbitan may be used as a base material.

The cosmetic composition may include other active ingredients in addition to 2,3-butanedil, and the active ingredient may be suitably modified or controlled according to the use, purpose, or formulation of the cosmetic composition.

In an embodiment, 2,3-butanediol may be utilized as the stabilizer of dispersant of the cosmetic composition. For example, if the cosmetic composition includes pigment particles, functional inorganic particles, or various natural particles, 2,3-butanediol may be utilized as an agent for improving the dispersibility and solubility of the particles.

In addition, 2,3-butanediol may be utilized as the surfactant of the cosmetic composition. For example, 2,3-butanediol may be used solely or in combination with other known surfactant components. The known surfactant may include nonionic surfactant, anionic surfactant, cationic surfactant, zwitterionic surfactant, etc.

The nonionic surfactant may use self-emulsifying glycerol monostearate, propylene glycol fatty acid ester, glycerin fatty acid ester, polyglycerin fatty acid ester, sorbitan fatty acid ester, polyoxyethylene (POE) sorbitan fatty acid ester, POE sorbit fatty acid ester, POE glycerin fatty acid ester, POE alkyl ether, POE fatty acid ester, POE hardened castor oil, POE castor oil, (polyoxyethylene.polyoxypropylene) POE.POP copolymer, POE.POP alkyl ether, polyether modified silicone, lauric acid alkanolamide, alkylamine oxide, hydrogen-added soybean phospholipid, etc.

The anionic surfactant may use fatty soap, α-acyl sulfonate, alkyl sulfonate, alkyl allyl sulfonate, alkyl naphthalene sulfonate, alkyl sulfate, POE alkyl ether sulfate, alkylamide sulfate, alkyl phosphate, POE alkyl phosphate, alkylamide phosphate, alkyloylalkyl taurinate, N-acylamino acid salt, POE alkyl ether carboxylate, alkyl sulfosuccinate, sodium alkyl sulfoacetate, acylation hydrolysis collagen peptide salt, perfluoroalkyl phosphoric acid ester, etc.

The cationic surfactant may use alkyltrimethylammonium chloride, stearyltrimethylammonium chloride, stearyltrimethylammonium bromide, cetostearyltrimethylammonium chloride, distearyldimethylammonium chloride, stearyldimethylbenzylammonium chloride, behenyl trimethyl ammonium bromide, benzalkonium chloride, stearic acid diethylaminoethylamide, stearic acid dimethylaminopropylamide, lanolin derivatives quaternary monium salt, etc.

The zwitterionic surfactant may use carboxybetaine type, amidebetaine type, sulfobetaine type, hydroxysulfobetaine type, amidesulfobetaine type, phosphobetadine type, aminocarboxylate type, imidazoline derivative type, amideamine type, etc.

In an embodiment, 2,3-butanediol may be used as a controller for controlling the physical properties of the cosmetic composition. For example, 2,3-butanediol may be utilized as a component or agent for controlling the viscosity or pH of the cosmetic composition to desired ranges.

In addition, 2,3-butanediol may be mixed with other diols and used. The other diol may include, for example, 1,3-propanediol, 1,3-butanediol, hexanediol, pentanediol, etc. In addition, 2,3-butanediol may be mixed with other polyols such as triol and used.

In case of using the alcohol mixture, 2,3-butanediol may be included in the largest amount. In addition, 2R,3S-butanediol or 2R,3R-butanediol may be included in the largest amount (for example, 90 wt % or more among the total weight of the alcohol mixture).

In some embodiments, for example, if at least one of 2R,3S-butanediol and 2R,3R-butanediol is used as an anti-inflammatory formulation, anti-oxidative formulation, or anti-wrinkle formulation, the one may be included as a single component.

Hereinafter, the use of 2,3-butanediol according to embodiments of the present invention will be explained in detail referring to particular experimental embodiments. Embodiments and comparative embodiments included in the experimental embodiments are only illustrations of the present invention but do not limit the attached claims. It is apparent that a person skilled in the art may make various changes and modifications on the embodiments within the scope of the present invention and technical spirit, and such modifications and changes are definitely included in the attached claims.

In the experimental embodiments below, as the 2,3-butanediol, a cassava raw material was used, and bio-based products through a fermentation product utilizing *Klebsiella oxytoca* (including 2R,3S-butanediol and 2R,3R-butanediol) were used, in common.

1) Experimental Example 1: Evaluation of Anti-Inflammatory Effects of 2,3-butanediol Anti-inflammatory effects were decided by the production inhibition ratio of nitric oxide (NO) when treating RAW 264.7 cells with lipopolysaccharide (LPS, NO production inducing material).

In order to evaluate the anti-inflammatory effects of 2,3-butanediol, the NO production inhibition ratio was measured using a Griess reagent analysis method. Particularly, the NO production inhibition ratio was measured by Equation 1 below.

NO production inhibition ratio (%)=[(absorbance of specimen treated group−absorbance of specimen untreated group)/(absorbance of negative control group−absorbance of specimen untreated group)]×100 [Equation 1]

i) specimen untreated group: group treated with a culture medium ii) specimen treated group: group treated with specimen by each concentration diluted with a culture medium and LPS iii) negative control group: group treated with a culture medium and LPS RAW 264.7 cell culture medium specimens including 1 wt % of each of 2R,3S-butanediol and 2R,3R-butanediol were prepared, and each specimen was treated with LPS, and absorbance was measured. Calculated NO production inhibition ratios are shown in Table 1 below.

TABLE 1

| Material name | Concentration (wt %) | NO production inhibition ratio (%) |
|---|---|---|
| 2R,3S-butanediol | 1.0 | 13.71 |
| 2R,3R-butanediol | 1.0 | 24.03 |

Referring to Table 1 above, each of 2R,3S-butanediol and 2R,3R-butanediol showed 10% or more of NO production inhibition ratio, and through this, anti-inflammatory effects were confirmed.

2) Experimental Example 2: Evaluation of Anti-Oxidative Effects of 2,3-butanediol To evaluate the anti-oxidative effects of 2,3-butanediol, the elimination activity of free radicals was measured using a 2,2-diphenyl-1-picrylhydrazyl (DPPH) analysis method. Particularly, an anti-oxidation ratio was calculated by Equation 2 below.

Anti-oxidation ratio (%)=[[(absorbance of specimen treated group−absorbance of specimen untreated group)/(absorbance of negative control group−absorbance of specimen untreated group)]×100 [Equation 2]

i) specimen untreated group: group allowing reaction of ultrapure water and methanol ii) specimen treated group: group allowing reaction of specimen by each concentration and DPPH iii) negative control group: group allowing reaction of ultrapure water and DPPH According to the concentration shown in Table 2 below, diols were diluted with a methanol solvent to prepare specimens, and each specimen was reacted with DPPH, and absorbance was measured, and the anti-oxidation ratios calculated are shown in Table 2 below.

TABLE 2

| Material name | Concentration (wt %) | Anti-oxidation ratio (%) |
|---|---|---|
| 2R,3S-butanediol | 0.1 | 2.23 |
| | 0.5 | 3.95 |
| | 1.0 | 5.12 |
| 1,3-butanediol | 0.1 | 2.89 |
| | 0.5 | 1.46 |
| | 1.0 | 1.00 |
| 1,3-propanediol | 0.1 | 5.34 |
| | 0.5 | 2.17 |
| | 1.0 | −1.23 |

Referring to Table 2 above, the anti-oxidation ratio was increased according to the increase of the concentration of 2R,3S-butanediol from 0.1 wt % to 1 wt %. In contrast, with the increase of the concentrations of 1,3-butanediol and 1,3-propanediol, the anti-oxidation ratio was rather decreased with the increase of the concentration. In addition, 2R,3S-butanediol with 1 wt % showed better anti-oxidation capacity than 1,3-butanediol and 1,3-propanediol.

3) Experimental Example 3: Evaluation of Anti-Wrinkle Effects of 2,3-butanediol

The anti-wrinkle effects of 2,3-butanediol were evaluated as the restraining effects of the decomposition of interstitial collagen, etc., by decreasing skin collagenase (for example, MMP-1).

To evaluate the anti-wrinkle effects of 2,3-butanediol, serum-free mediums composed of 99 mL of Dulbecco's modified eagle medium (Gibco) and 1 mL of Penicillin-streptomycin (Gibco), diluted with 2R,3S-butanediol, 2R,3R-butanediol, 1,3-butanediol and 1,3-propanediol in the concentrations shown in Table 3 below, were prepared.

TABLE 3

| | Material name | Concentration (wt %) |
|---|---|---|
| Example 1 | 2R,3S-butanediol | 0.05 |
| Example 2 | | 0.10 |
| Example 3 | | 0.50 |
| Example 4 | | 1.00 |
| Example 5 | 2R,3R-butanediol | 0.05 |
| Example 6 | | 0.10 |
| Example 7 | | 0.50 |
| Example 8 | | 1.00 |
| Comparative Example 1 | 1,3-butanediol | 0.50 |
| Comparative Example 2 | 1,3-propanediol | 0.50 |

In addition, cells CCD-986SK (ACTT CRL-6323™) were seeded in well plates by 1 mL with $5\times10^4$, and cultivated at 37° C. in a 5% $CO_2$ cultivator for 24 hours. The cultivated cells were replaced with the mediums of the Examples and Comparative Examples and cultivated at 37° C. in a 5% $CO_2$ cultivator for 48 hours.

A cell dissolution material was recovered, the protein content was measured using BSA protein assay reagent kit (Thermo scientific PIERCE, USA), the collagenase (MMP-1) content was measured suing Human MMP-1 ELISA kit (Sigma), and the results are shown in Table 4 below.

A collagenase activity restraining ratio in cells was calculated by Equation 3 below and shown in Table 4 below. That is, the decreased percent calculated means that collagenase is effectively restrained.

[Equation 3]

$$\text{Collagenase restraining ratio in cells (\%)} = \frac{\text{specimen added group (collagenase/protein)}}{\text{specimen-free group (collagenase/protein)}} \times 100$$

TABLE 4

| | Collagenase (MMP-1)(pg/mL) | Protein (μg/mL) | Collagenase (MMP-1) restraining ratio (%) |
|---|---|---|---|
| Specimen-free | 650.7 | 211.37 | 100.00 |
| Example 1 | 370.2 | 199.83 | 60.78 |
| Example 2 | 364.7 | 198.54 | 59.80 |
| Example 3 | 324.2 | 187.33 | 56.69 |
| Example 4 | 321.4 | 165.90 | 62.63 |
| Example 5 | 390.9 | 201.41 | 56.16 |
| Example 6 | 443.0 | 199.74 | 63.45 |
| Example 7 | 327.7 | 186.85 | 50.73 |
| Example 8 | 159.1 | 168.73 | 27.29 |
| Comparative Example 1 | 569.1 | 203.25 | 90.82 |
| Comparative Example 2 | 602.9 | 207.90 | 94.23 |

Referring to Table 4 above, Examples using 2R,3R-butanediol and 2R,3S-butanediol showed markedly increased restraining effects of collagenase when compared with the Comparative Examples using 1,3-butanediol or 1,3-propanediol. Particularly, in case of 2R,3R-butanediol, the production of collagenase was markedly reduced at a concentration of 1 wt %.

The invention claimed is:

1. A method for treating skin wrinkles, the method comprising administering or applying a composition comprising 2,3-butanediol to a subject in need thereof,
   wherein the 2,3-butanediol consists of 2R,3R-butanediol, and the 2,3-butanediol is included in 1 to 10wt % based on the total weight of the composition, wherein the administering or applying comprises topically applying the composition to skin of the subject, and
   wherein the composition is formulated as a cream, lotion, gel, ointment. or emulsion.

2. The method of claim 1, wherein the 2,3-butanediol is derived from bio-mass.

3. The method of claim 1, wherein the 2,3-butanediol is derived from cassava raw material and *Klebsiella* strain.

4. The method of claim 1, wherein the composition is a pharmaceutical composition.

5. The method of claim 1, wherein the composition is a cosmetic composition.

* * * * *